(12) United States Patent
Biedermann et al.

(10) Patent No.: US 7,879,036 B2
(45) Date of Patent: Feb. 1, 2011

(54) BONE ANCHORING ELEMENT (75) Inventors: Lutz Biedermann, VS-Villingen (DE); Wilfried Matthis, Weisweil (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 269 days.

(21) Appl. No.: 11/499,034

(22) Filed: Aug. 4, 2006

(65) Prior Publication Data
US 2007/0073295 A1 Mar. 29, 2007

Related U.S. Application Data (60) Provisional application No. 60/706,073, filed on Aug. 5, 2005.

(30) Foreign Application Priority Data
Aug. 5, 2005 (EP) ................................. 05017115

(51) Int. Cl.
A61B 17/56 (2006.01)
A61B 17/58 (2006.01)
A61B 17/68 (2006.01)
A61B 17/72 (2006.01)
A61B 17/88 (2006.01)

(52) U.S. Cl. ............................ 606/62; 606/60; 606/63; 606/64; 606/246; 606/279; 606/300; 606/304; 606/307; 606/310; 606/313

(58) Field of Classification Search ............ 606/60–64, 606/72, 74, 139, 260–279, 300–321, 246
See application file for complete search history.

(56) References Cited
U.S. PATENT DOCUMENTS 4,331,423 A * 5/1982 Yanney, Jr. .................. 433/225
5,209,753 A * 5/1993 Biedermann et al. ........ 606/304
5,562,704 A 10/1996 Tamminmäki et al.
5,577,912 A * 11/1996 Prins .......................... 433/172
5,645,589 A * 7/1997 Li ................................. 606/60
6,183,474 B1 2/2001 Bramlet et al.
6,302,885 B1 10/2001 Essiger (Continued)

FOREIGN PATENT DOCUMENTS

CH              682450 A5     9/1993

(Continued)

OTHER PUBLICATIONS

European Search Report for European Application No. 05017115.6-2318 dated Dec. 6, 2005, 6pp.

*Primary Examiner*—Thomas C Barrett
*Assistant Examiner*—Sameh Boles
(74) *Attorney, Agent, or Firm*—Christie, Parker & Hale LLP (57) ABSTRACT

A bone anchoring element is provided which has a shaft for anchoring in a bone. The shaft includes a tubular body having two open ends. At least one barb element is connected to the shaft. The barb element is cut into the tubular body. The barb element includes a free end and a base connecting the barb element to the shaft. The barb element has a first portion adjacent to the base and a second portion adjacent to the free end. The second portion is inclined relative to the first portion in a direction off said shaft.

19 Claims, 10 Drawing Sheets

U.S. PATENT DOCUMENTS

| | | |
|---|---|---|
| 6,660,008 B1 * | 12/2003 | Foerster et al. .............. 606/327 |
| 2003/0045885 A1 | 3/2003 | Margulies et al. |
| 2004/0015172 A1 * | 1/2004 | Biedermann et al. .......... 606/73 |
| 2004/0122431 A1 | 6/2004 | Biedermann et al. |
| 2005/0159749 A1 * | 7/2005 | Levy et al. .................... 606/72 |
| 2005/0187555 A1 * | 8/2005 | Biedermann et al. .......... 606/72 |
| 2006/0264952 A1 * | 11/2006 | Nelson et al. ................. 606/72 |

FOREIGN PATENT DOCUMENTS

| | | |
|---|---|---|
| DE | 19801219 A1 | 7/1999 |
| EP | 0714643 A1 | 6/1996 |
| FR | 2 731 610 | 9/1996 |
| FR | 2731610 A1 | 9/1996 |

* cited by examiner

BONE ANCHORING ELEMENT

RELATED APPLICATIONS

The present application claims the benefit of U.S. Provisional Patent Application Ser. No. 60/706,073, filed Aug. 5, 2005, and claims priority from European Patent Application EP05017115.6, filed Aug. 5, 2005, the entire disclosures of which are incorporated herein by reference.

BACKGROUND

The present disclosure relates to a bone anchoring element having barb elements connected to its shaft and a method for producing the same.

EP 0 714 643 A1 discloses a bone fixation device such as a screw, pin, staple, cable or anchor which has a micro-textured contact surface to enhance the installation or gripping characteristics of the device. The micro-textured contact surface includes features with directional asymmetry or angled suspension, e.g. angled rasp teeth, which bite or flex to resist movement in one direction and yet flex or slide to allow a relatively easy contact movement in the other direction.

DE 198 01 219 A1 discloses a bone nail having rigid barb-like projections being arranged in circumferential rows around the nail. The barb-like projection has a saw-tooth shape which not only facilitates insertion of the nail but also prevents the nail from loosening. However, removing the nail without destroying the bone is impossible.

CH 682 450 A5 discloses an anchoring nail for the fixation of orthopedic bone implants. The nail consists of a head part and a shaft part, the shaft having retention elements provided on its outer wall which are arranged along a helical line. The retention elements are wedge-shaped and are provided with cutting edges which allow to screw out and remove the nail from the bone material. However, the core hole which has to be drilled in advance has to have a precise diameter to allow both an easy insertion of the nail into the bone as well as the removal of the nail. In addition, the wedge-shape of the retention elements per se does not allow an easy insertion.

U.S. Pat. No. 5,562,704 describes a surgical implant of a polymer. The implant contains arresting members for arresting the implant in a position in a direction opposite to the direction of installation. The arresting members are formed in a direction substantially parallel to the body.

In view of the above, there is a need for a bone anchoring element that can remedy one or more of the above described problems associated with current bone anchoring elements.

SUMMARY

A bone anchoring element according to one or more embodiments of the present disclosure can be inserted into the bone more rapidly, more easily and with less force than conventional bone screws and nails. The bone anchoring element according to one or more embodiments of the present disclosure is versatile and useful for many clinical requirements and is easy to manufacture. The bone anchoring element according to one or more embodiments of the present disclosure does not exert damaging forces on the bone during insertion and provides for secure attachment. A method for manufacturing such a bone anchoring element is also disclosed.

A bone anchoring element according to one or more embodiments of the present disclosure facilitates rapid and secure anchoring to the bone by pressing the bone anchoring element into a core hole provided in the bone. The barb elements can prevent the bone anchoring element from being pulled out or becoming loose. If the bending line of the barb elements is nearer to the free end than to the base, the insertion force is reduced while the pull out force is increased. The barb elements may be arranged on at least one helical line around the shaft axis of the bone anchoring element. The barb elements provide for a thread-like function, which allows to correct the position of the bone anchoring element in the core hole after inserting it into the core hole, by either positioning it deeper into the bone by means of a screwing-inwards motion or by screwing it backwards. The bone anchoring element can be removed, if required, like a screw by turning it in the direction opposite or counter-clockwise the insertion direction.

The bone anchoring element according to one or more embodiments of the present disclosure is easy to manufacture. If the barb elements are made of a shape memory alloy, the shape memory effect can be used in such a way that the barb elements do not project during insertion of the bone anchoring element into the bone and rise up when the bone anchoring element is inserted due to the action of the body heat. The barb elements can also be made of a material having superelastic properties or a spring like behaviour. For example a titanium alloy having superelasticity or stainless steel can be used.

Further features and advantages of the present disclosure will become apparent and will be best understood by reference to the following detailed description taken in conjunction with the accompanying drawings.

DETAILED DESCRIPTION

A bone anchoring element according to a first embodiment of the disclosure is described with reference to FIGS. 1 to 5. The bone anchoring element 1 comprises a shaft 2 with a tip 3 at one end and a head 4 at the other end. The head 4 is spherical segment-shaped and has on its free end a recess 5 for engagement with a screwing-in tool. Adjacent to the head 4 is a first cylindrical portion 6. The first cylindrical portion 6 has an outer diameter which is slightly smaller than the diameter of the head 4. Adjacent to the first cylindrical portion 6, at a side opposite to the head 4, a second cylindrical portion 7 is provided. The diameter of the second cylindrical portion 7 is smaller than that of the first cylindrical portion 6 such that a step is formed. Adjacent to the second cylindrical portion 7, a cylindrical shaft part 8 is provided. The diameter of the cylindrical shaft part 8 is smaller than that of the second cylindrical portion 7. At the edge of the first cylindrical portion 6, facing the shaft part 8, a plurality of U-shaped recesses 9 are provided equidistantly in a circumferential direction which are open towards the side of the cylindrical shaft part 8.

Figure 1:
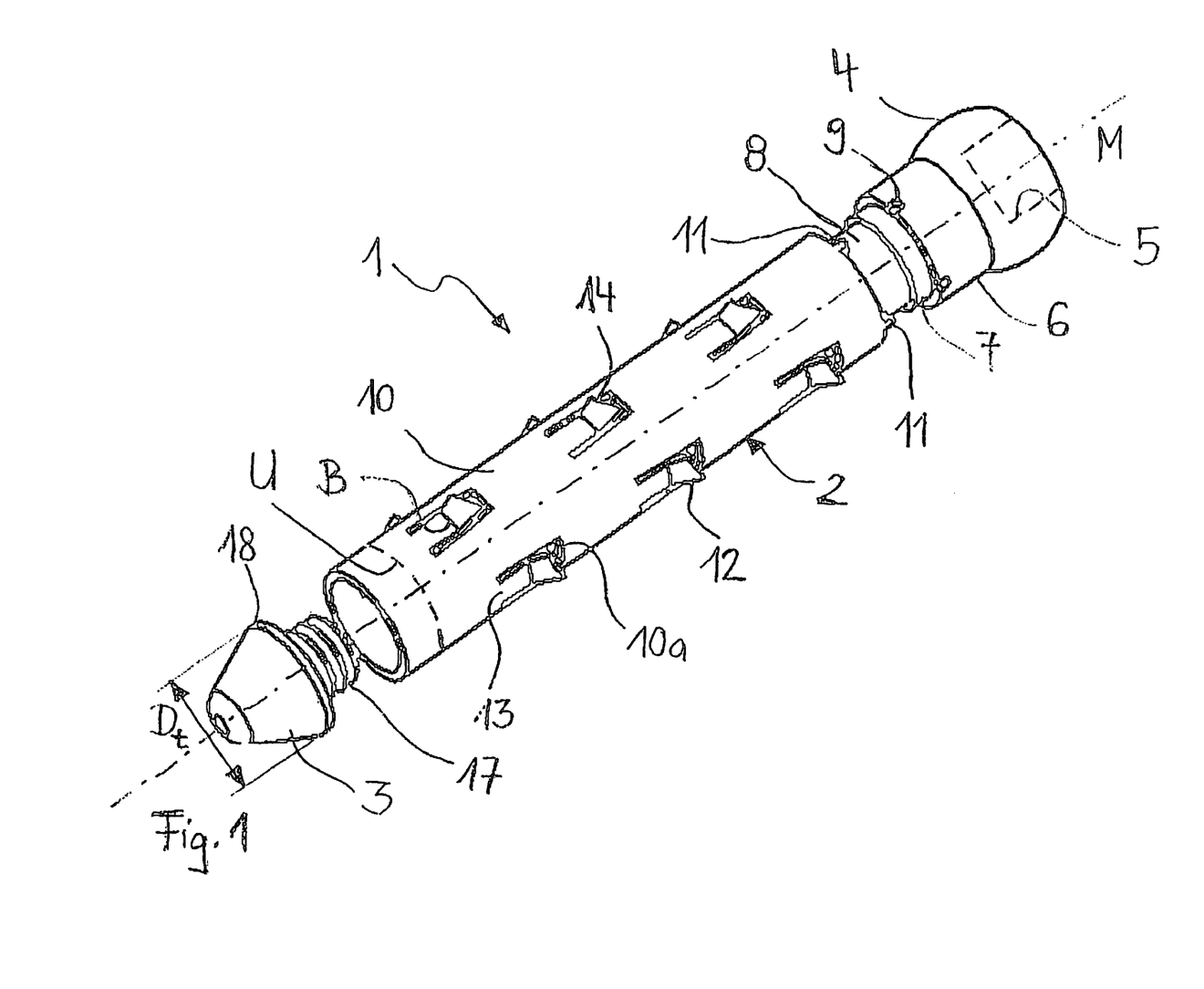
FIG. 1 shows a perspective exploded view of a bone anchoring element according to a first embodiment.
Figure 3:
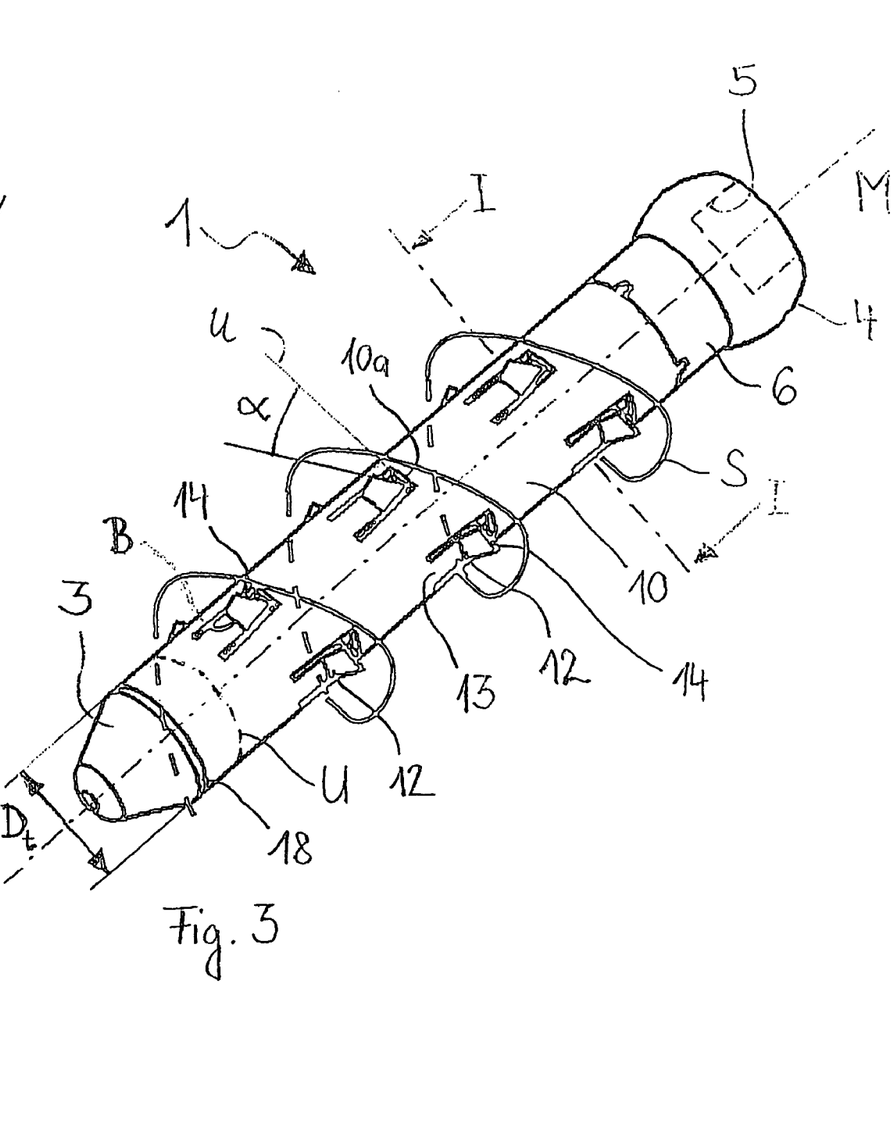
FIG. 3 shows a perspective view of the bone anchoring element according to FIG. 1 in an assembled state.
Figure 4:
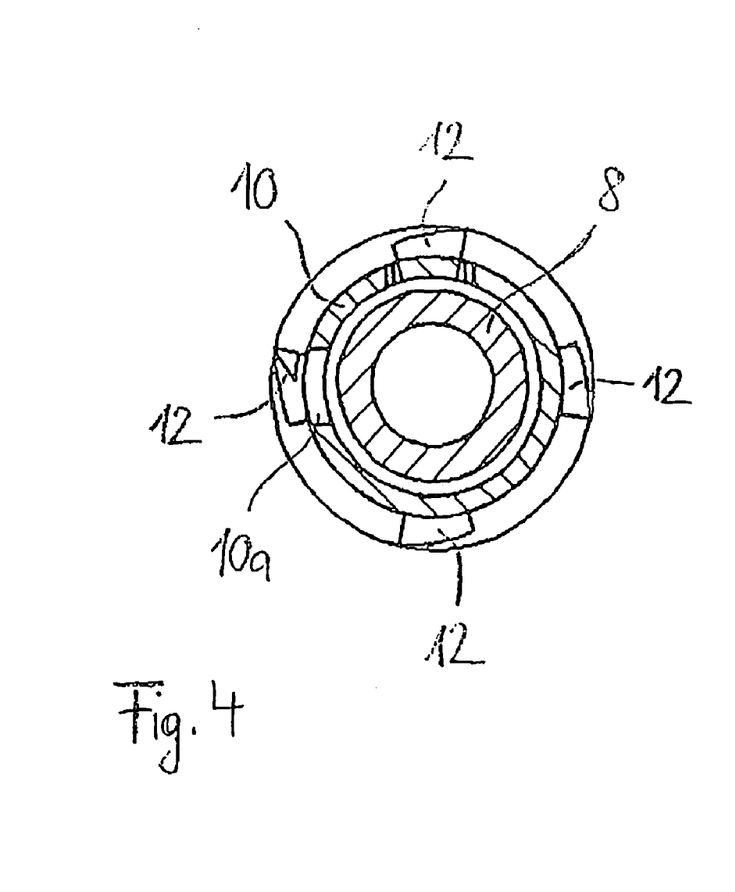
FIG. 4 shows a cross-sectional view of the bone anchoring element of FIG. 3 along the line I-I.

The shaft 2 further includes a tubular body 10 which has an inner diameter slightly larger than the outer diameter of the second cylindrical portion 7, so that the tubular body 10 can be placed onto the cylindrical shaft part 8 and the second cylindrical portion 7. The outer diameter of the tubular body 10 corresponds to the outer diameter of the first cylindrical portion 6, so that when the tubular body 10 is placed onto the shaft part 8, the outer surface of the tubular body 10 is flush with the outer surface of the first cylindrical portion 6. On its end facing the head 4, the tubular body 10 has projections 11 which correspond in their shape and arrangement to the U-shaped recesses 9 provided at the edge of the first cylindrical portion 6 for engagement when the tubular body 10 is fully placed onto the cylindrical shaft part 8. As can be seen in FIG. 3, in the assembled state, the end of the tubular body 10 abuts the free end of the first cylindrical portion 6.

Figure 2:
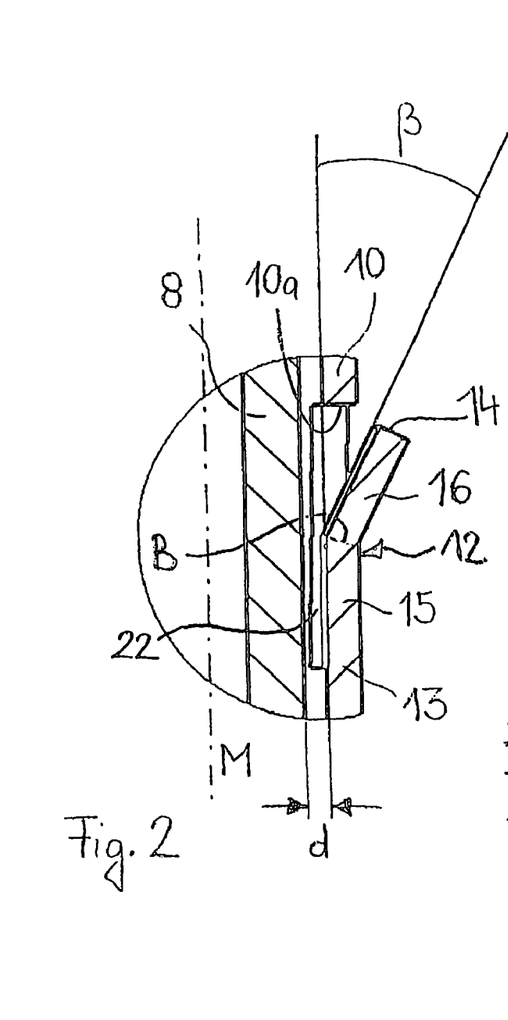
FIG. 2 shows an enlarged part of a cross-sectional view through the bone anchoring element of FIG. 1 in a longitudinal direction.

In the assembled state, as can be seen in FIG. 2, the tubular body 10 is spaced from the shaft part 8 by a distance d, which is identical to the difference of the radius of the second cylindrical portion 7 and the shaft part 8.

The tubular body 10 comprises a plurality of barb elements 12. The barb elements 12 are formed by cuts 10a being made in the wall of the tubular body 10. The cuts 10a may be substantially quadrangular cuts. The base 13 of the cuts 10a is not cut-out from the tubular body and acts as the attachment for the barb elements 12 to the wall of the tubular body 10. The barb elements 12 are preferably arranged such that when the tubular body 10 is placed onto the cylindrical shaft part 8, the base 13 of the barb elements 12 faces the tip 3, while the free end 14 faces the head 4. As can be seen particularly in FIG. 3, the barb elements 12 are arranged on a helical line S around the shaft axis M. The free ends 14 of the barb elements are inclined by an angle α with regard to the circular circumference line U, with the angle α corresponding to the helical angle of the helical line S. Thus, the free ends 14 of the barb elements 12 form cutting edges similar to the crest of a screw thread.

As can be seen in particular from FIG. 2, the barb elements 12 have, adjacent to their base 13, a base portion 15 parallel to the main axis M of the shaft. A free end portion 16 of the barb elements 12 is bent away from the shaft 2 at an angle β, so that it is inclined to the base portion 15 at the angle β. The angle β is selected during the manufacturing process depending on the material used and on the actual dimensions of the barb elements 12 so that a desired stiffness of the barb element 12 is obtained. The base portion 15 and the free end portion 16 are substantially flat. Due to their configuration and attachment onto the wall of the tubular body 10, the barb elements 12 are elastically deformable relative to the tubular body 10. A hollow space 22 is defined in the shaft between the base portion 15 and the shaft part 8 to allow the base portion 15 to be elastically deformed and pivoted towards the shaft axis M. When the barb elements 12 are collapsed or pressed into the cuts, i.e., the hollow space 22, they are pre-tensioned.

Figure 5:
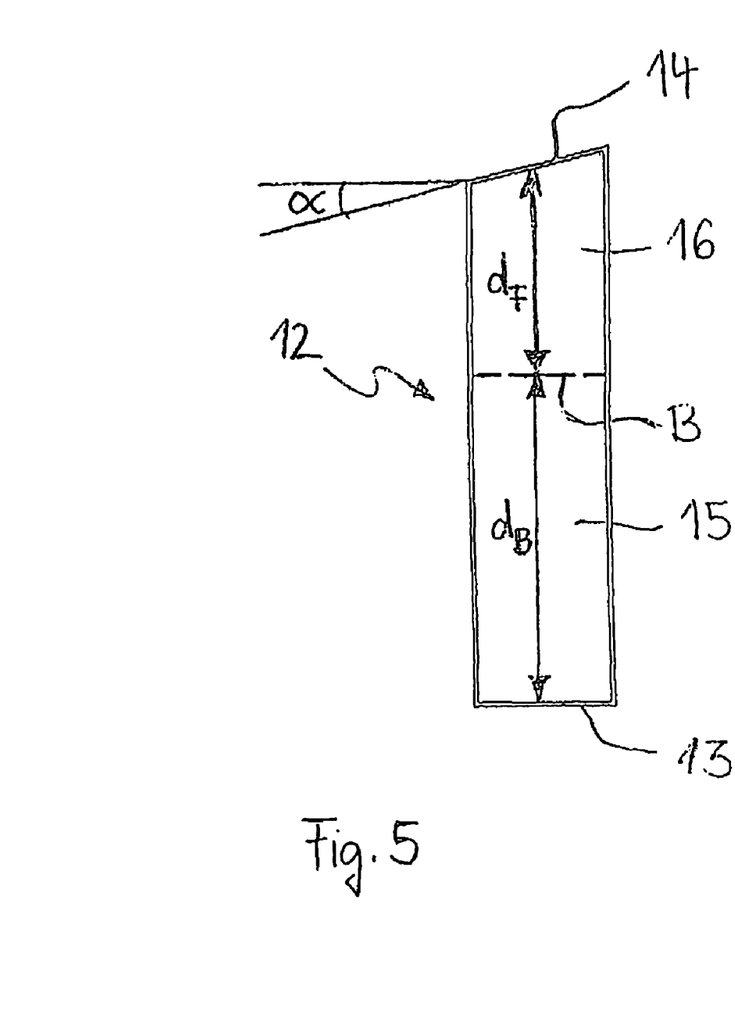
FIG. 5 shows a schematic top view of a barb element of the bone anchoring element according to the first embodiment.

FIG. 5 shows a schematic top view of a single barb element 12. The free end 14 of the barb element is inclined at the angle α with regard to the circumferential line U to form a cutting edge like the part of a crest of a screw thread. The bending line B at which the free end portion 16 of the barb element 12 is bent away from the shaft 2 is located nearer to the free end 14 than to the base 13, i.e., the mean distance $d_f$ of the bending line B to the free end 14 is smaller than the mean distance $d_b$ of the bending line B to the base 13. Preferably, the mean distance $d_f$ is about half of the mean distance $d_b$.

The axial length of the tubular body 10 is such that in an assembled state, the free end of the cylindrical shaft part 8 is flush with the free end of the tubular body 10. The cylindrical shaft part 8 has a cylindrical bore (not shown) at its free end with a female thread to receive a correspondingly shaped cylindrical projection 17 with a male thread provided at the tip 3. The outer diameter $D_t$ of the base 18 of the tip 3 corresponds to the outer diameter of the tubular body 10 so that in an assembled state, as shown in FIG. 3, the base 18 of the tip 3 is flush with the outer wall of the tubular body 10.

The bone anchoring element 2 can be made of any body-compatible material. Preferably, a body-compatible metal, such as titanium, stainless steel and their alloys, or a body-compatible plastic material can be used. The tubular body 10 having the barb elements 12 can be made of the same material as the shaft part 8, the head 4 and the tip 3 or of a different material if a different material is desired to ensure that the barb elements 12 have the necessary elastic properties.

Preferably, the tubular body 10 with the barb elements 12 is made of a shape memory alloy having shape memory and/or super elastic characteristics, or it is made of a material having spring-like characteristics like stainless steel or titanium alloys. For example, nickel titanium alloys such as nitinol are suitable for use for the tubular body 10.

In operation, the bone anchoring element 1 is initially preassembled by placing the tubular body 10 onto the shaft part 8 such that the projections 11 come into engagement with the recesses 9. Thus, a rotation of the tubular body 10 on the cylindrical shaft part 8 is prevented. Thereafter, the tip 3 is screwed into the bore at the free end of the shaft part opposite to the head 4. In use, as is shown schematically in FIGS. 6 and 7, first a core hole 19 is prepared in the bone 20. The diameter of the core hole 19 corresponds essentially to the outer diameter of the tubular body 10 or it can be slightly larger or smaller, depending upon the desired result or circumstances. The diameter $d_c$ of the core hole 19 is selected depending on the diameter of the tubular body 10 and the flexibility of the barb elements 12 so that the desired resistance is provided by the barb elements 12. The selected diameter $d_c$ depends also upon the bone quality, for example, it can be selected larger for healthy hard bone and smaller for osteoporotic weak bone.

Figure 6:
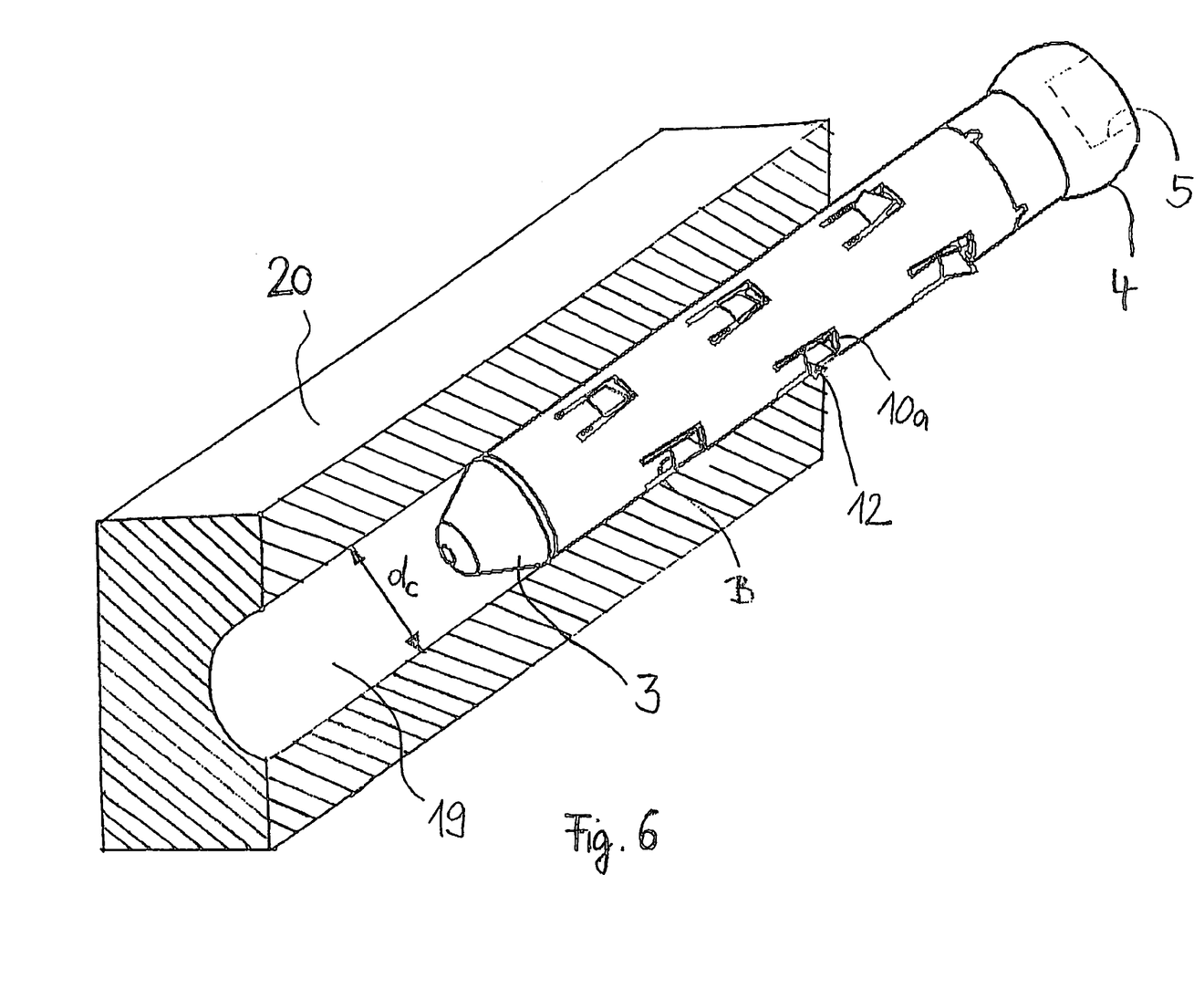
FIG. 6 shows a schematic view of a first step of insertion of the bone anchoring element according to FIG. 1-4.
Figure 7:
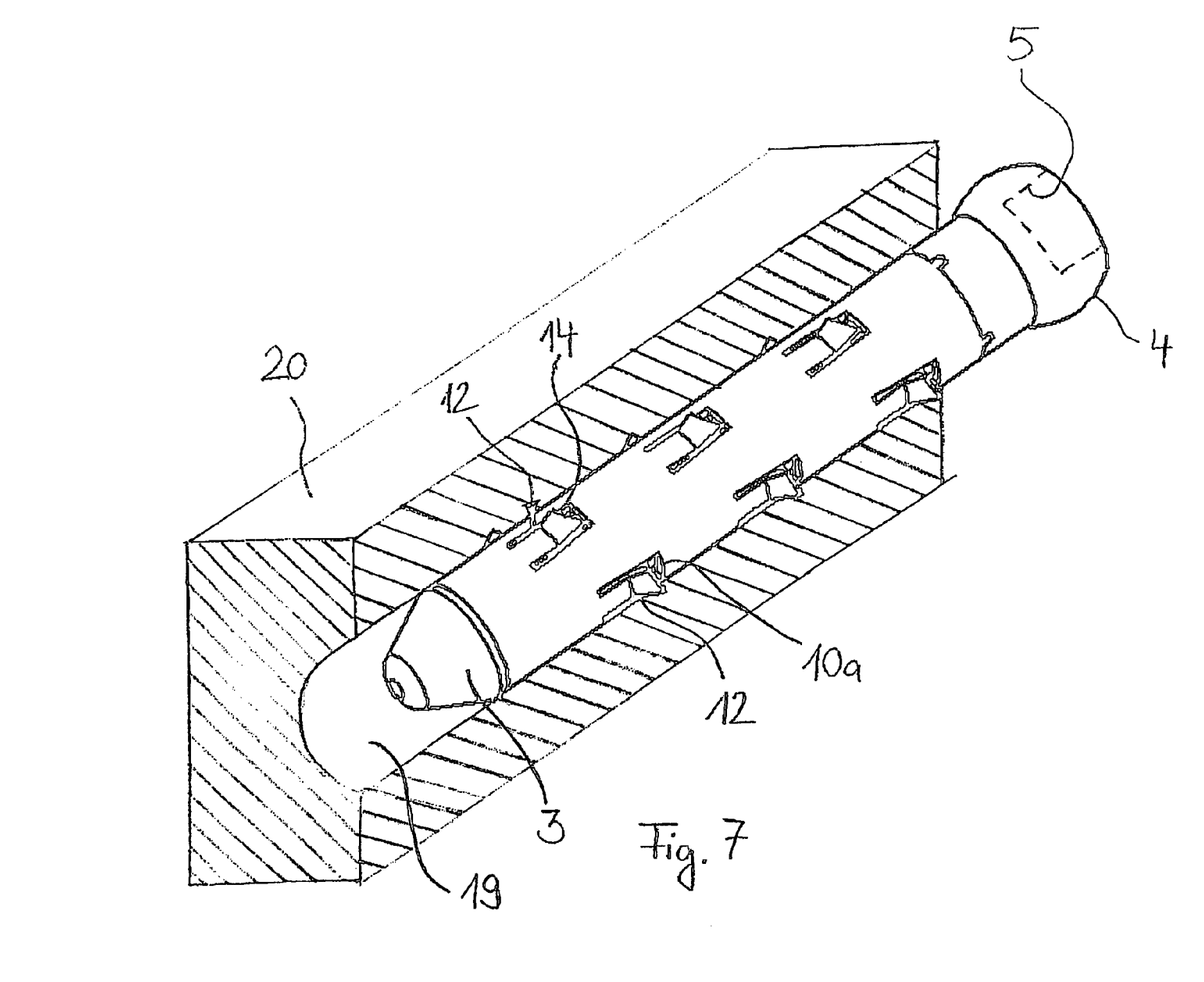
FIG. 7 shows a schematic view of the inserted state of the bone anchoring element according to FIG. 6.

Subsequently, as shown in FIG. 6, the bone anchoring element 1 is inserted into the core hole 19. As the bone anchoring element is being inserted into the core hole 19 of the bone 20, the barb elements 12 are in a collapsed state and are pressed against or into their corresponding hollow spaces 22 due to their elasticity. The sliding motion enables the bone anchoring element 1 to be inserted rapidly and in a smooth way, in contrast to the conventional bone screws using the screwing-in-process. When inserted, the pre-tensioned barb elements 12 expand and rise up and press with their cutting edges 14 outwardly against the wall of the core hole 19, as is shown in FIG. 7. The barb elements 12 prevent the bone anchoring element 1 from being pulled out or from falling out of the core hole 19.

For further and/or final positioning of the bone anchoring element 1 in the core hole 19, or for positioning of the head 4, the bone anchoring element 1 is screwed further into the core hole 19 or screwed out therefrom, like a screw, by means of a turning motion with the screwing-in tool engaging the recess 5 in the head 4. During the process, the cutting edges 14 of the barb elements 12, being positioned on the helical line S, act like the crest of a thread. The bone anchoring element 1 can be removed just like a bone screw by turning it in a counterclockwise direction.

Figure 8A:
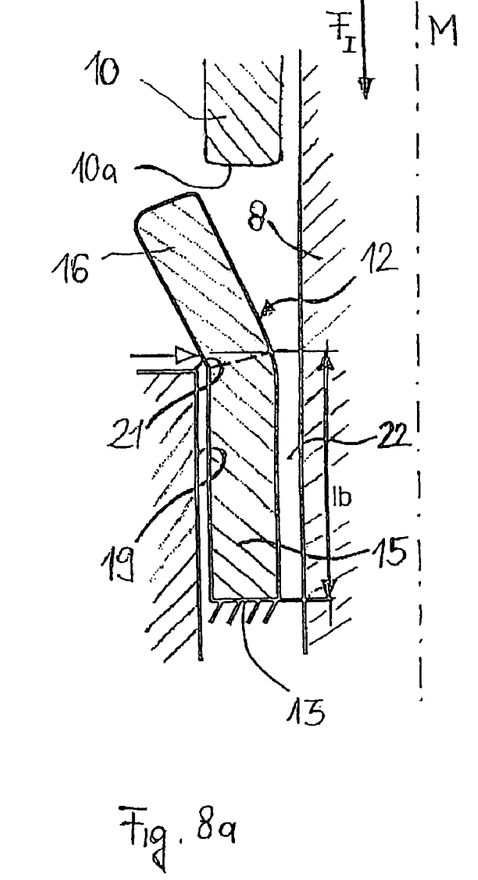
FIGS. 8a-8c show a schematic side view of the barb element of FIG. 5 during insertion of the bone anchoring element into the core hole.
Figure 8B:
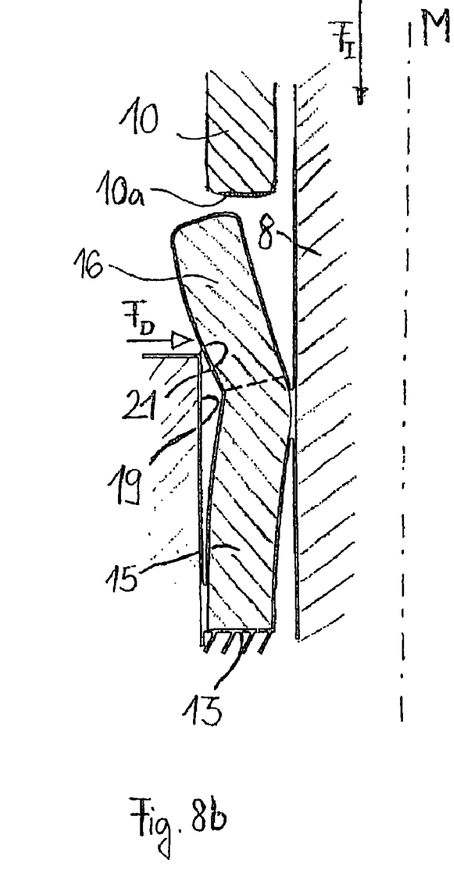
Figure 8C:
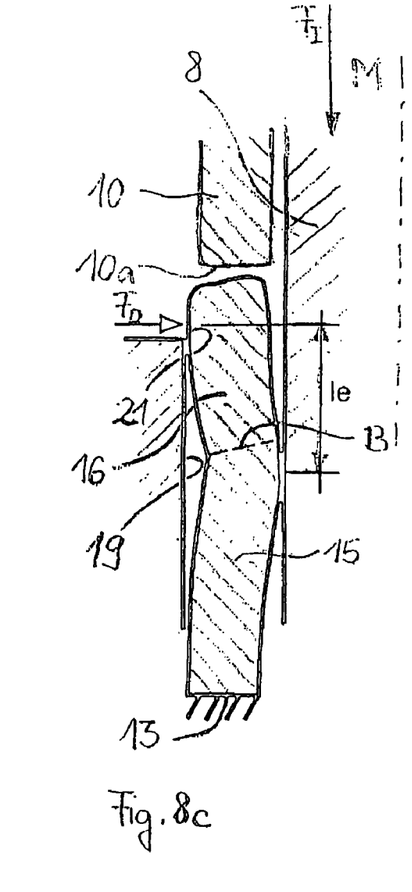

FIGS. 8a to 8c show a single barb element 12 of the bone anchoring element 1 according to the first embodiment in different states during insertion of the bone anchoring element 1 into a core hole 19. In FIG. 8a only the base portion 15 of the barb element 12 is inserted into the core hole 19, the free end portion 16 of the barb element 12 is still outside of the core hole 19. Because the base portion 15 of the barb element 12 does not project out of the cut 10a of the tubular body 10, there is no force acting on the barb element 12 in this phase of insertion. When the edge 21 of the core hole 19 comes into contact with the free end portion 16 of the barb element 12, i.e. when the bending line B of the barb element 12 passes into the core hole 19, the barb element is elastically deformed and pivoted towards the shaft part 8. The base portion 15 acts as a lever arm having a length 1b. Due to the lever arm 1b, the force $F_I$ necessary for pressing the barb element into the cut 10a is low compared to a case where the bending line B is located at the base 13. Hence, if the base portion 15 is oriented in parallel to the main axis M of the shaft 2, the force $F_I$ necessary for insertion of the bone anchoring element 1 into the core hole 19 is reduced. After being inserted further, the base portion 15 of the barb element 12 abuts against the shaft part 8 as can be seen in FIG. 8b. Then, the lever arm 1e determines the force $F_D$ necessary to further deform the barb element 12 and, therefore, it determines also the force $F_I$ necessary to insert the bone anchoring element 1 into the core hole 19.

By providing the barb element 12 with a base portion 15 parallel to the shaft axis M and a free end portion 16 bent outwards from the shaft 2, it is possible to lower the force $F_I$ necessary for insertion without lowering the force which is necessary for pulling out the bone anchoring element 1 from the core hole 19 after insertion.

A process for manufacturing the bone anchoring element 2 includes providing a cylinder having a diameter corresponding to that of the tubular body 10. The cylinder can be made of a material which is desired for the tubular body 10, preferably a shape memory alloy or another metallic material or an alloy with flexible properties. In a next step, a coaxial bore is provided in the cylinder such that a tubular body 10 is prepared. Thereafter, the barb elements 12 are generated by means of cutting, for example laser cutting, quadrangular cuts in the wall of the tubular body 10 in which one side which shall be the base of the barb elements 12 is not cut out. Then, the barb elements 12 are bent so as to project to the outside, wherein the bending line B is nearer to the free end 14 of the barb element 12 than to its base 13.

Figures 9, 10:
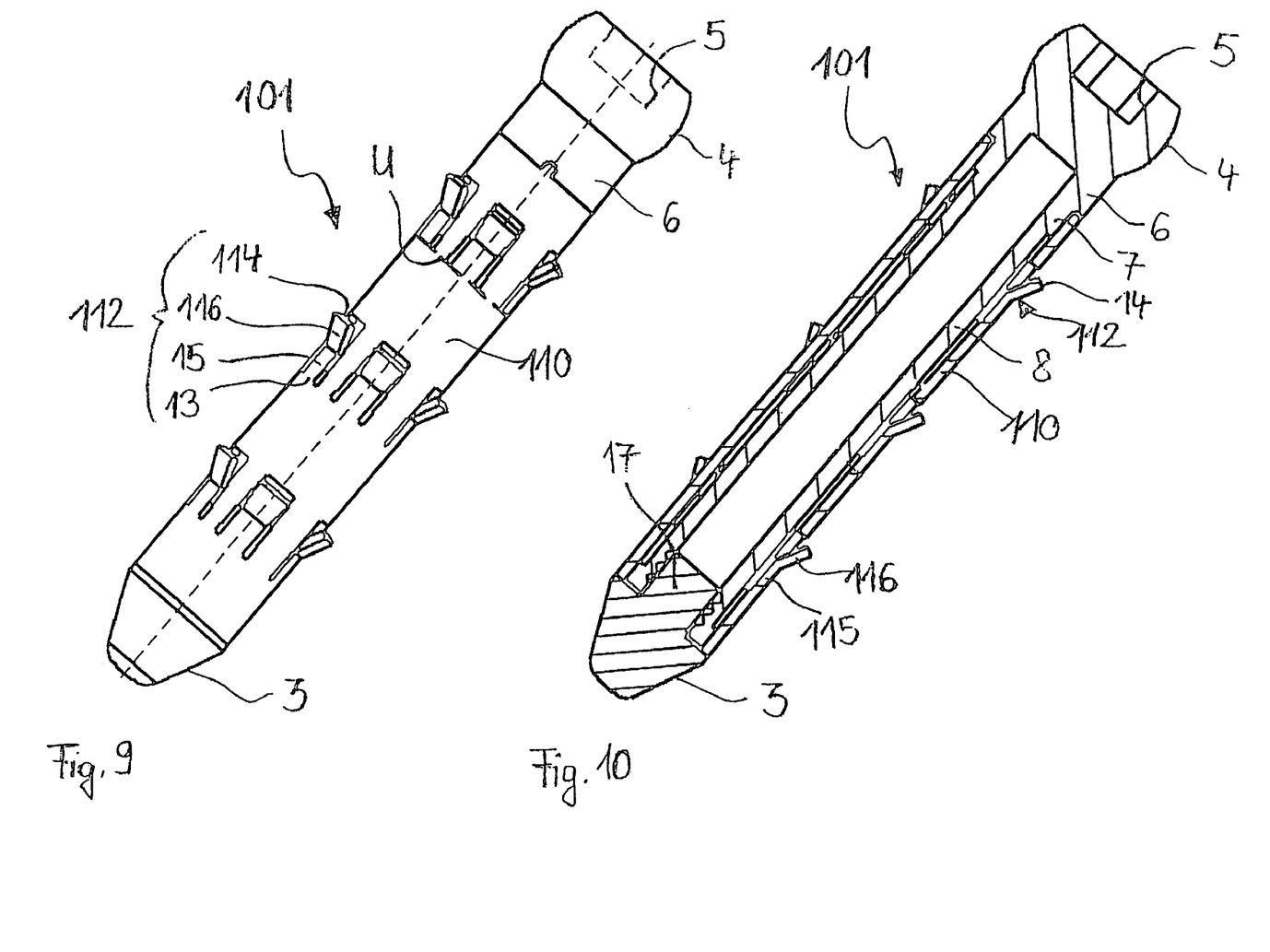
FIG. 9 shows a side view of a bone anchoring element according to a second embodiment.
FIG. 10 shows a cross-sectional view through the bone anchoring element of FIG. 9 in a longitudinal direction.

In the second embodiment shown in FIGS. 9 and 10, those parts which correspond to the parts of the first embodiment are characterized with the same reference numerals. FIG. 9 is a side view of the bone anchoring element 101 according to the second embodiment, and FIG. 10 is a cross-sectional view of the bone anchoring element 101 according to FIG. 9. The bone anchoring element 101 of the second embodiment differs from the bone anchoring element 1 according to the first embodiment in that the barb elements 112 do not provide for a thread-like function.

Accordingly, the barb elements 112 are not arranged along at least one helical line S but on at least one circumferential line U of the tubular body 110. The free end 114 of the free end portion 116 of the barb element 112 is perpendicular to the main axis M of the bone anchoring element 101.

Figure 11:
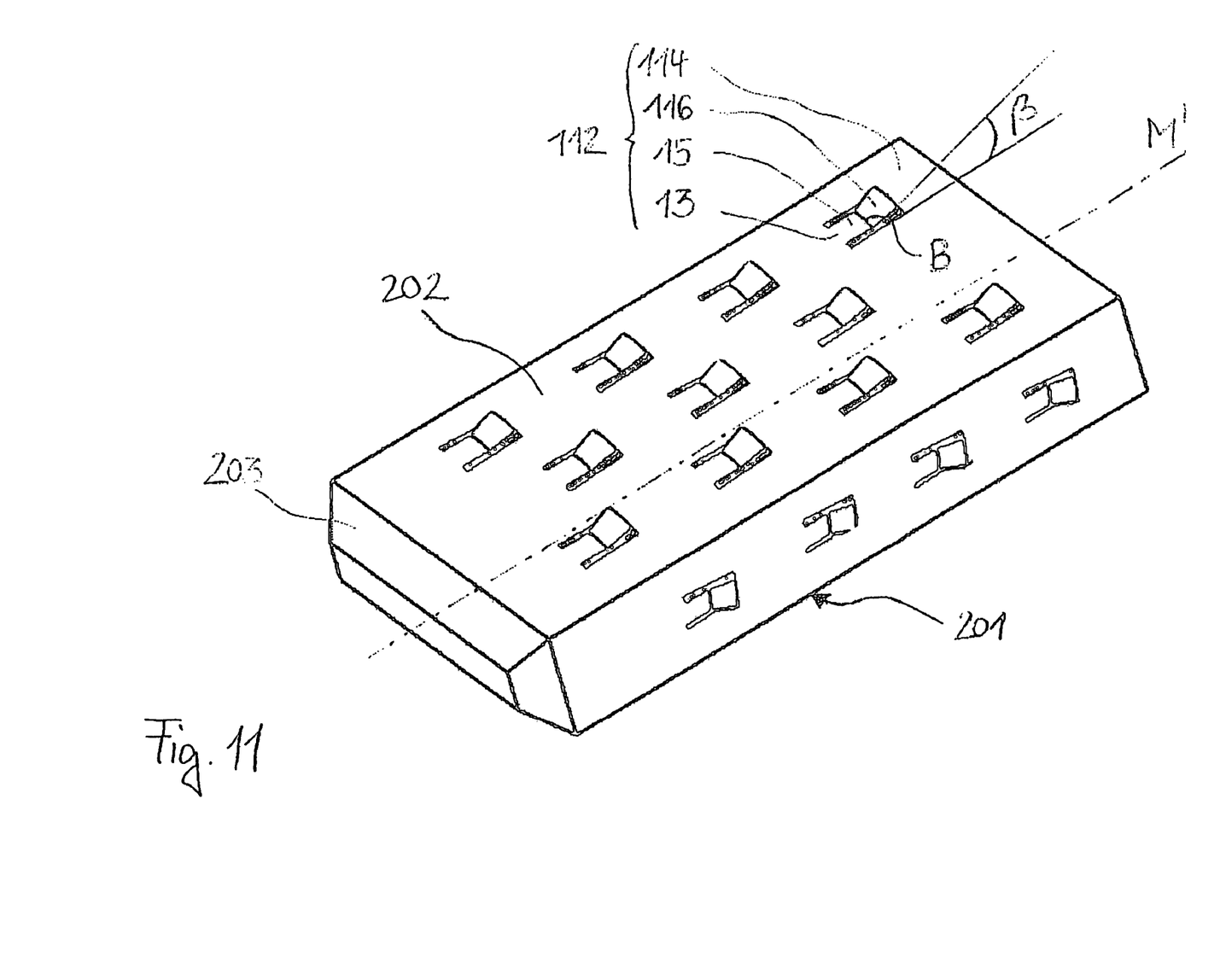
FIG. 11 shows a perspective view of a bone anchoring element according to a third embodiment.

In the third embodiment shown in FIG. 11, those parts which correspond to the parts of the second embodiment are characterized with the same reference numerals. FIG. 11 is a perspective view of the bone anchoring element 201 according to the third embodiment. The bone anchoring element 201 differs from the bone anchoring element according to the second embodiment in that the shaft 202 has a rectangular cross-section perpendicular to its main axis M'. At one end of the shaft 202 is a tip 203, which is formed in the shape of a flattened four sided pyramid. On its four side faces, the shaft has barb elements 112 which are formed like the barb elements of the second embodiment. The barb elements are arranged on lines parallel to the main axis M'. The barb elements are oriented such that the base 13 of the individual barb elements 112 faces the tip 203.

Figure 12A:
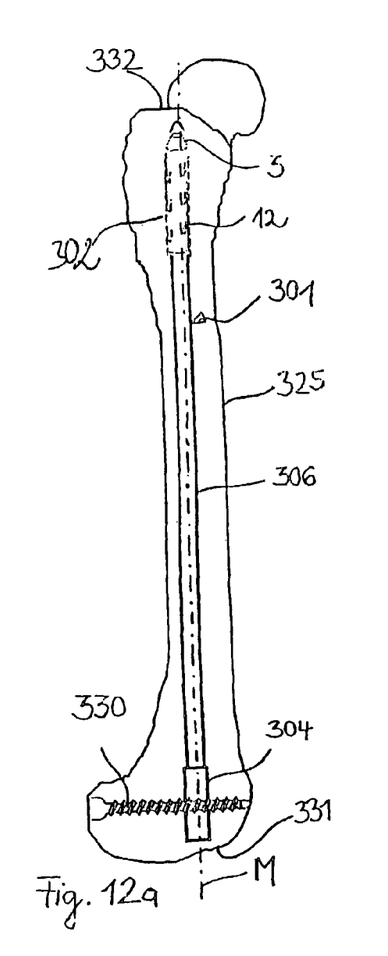
FIGS. 12a-12c show a bone anchoring element according to a fourth embodiment.
Figure 12B:
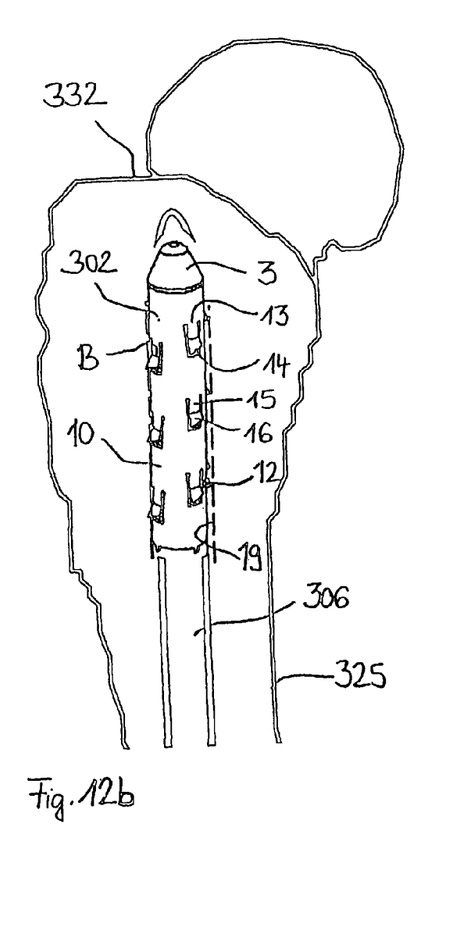
Figure 12C:
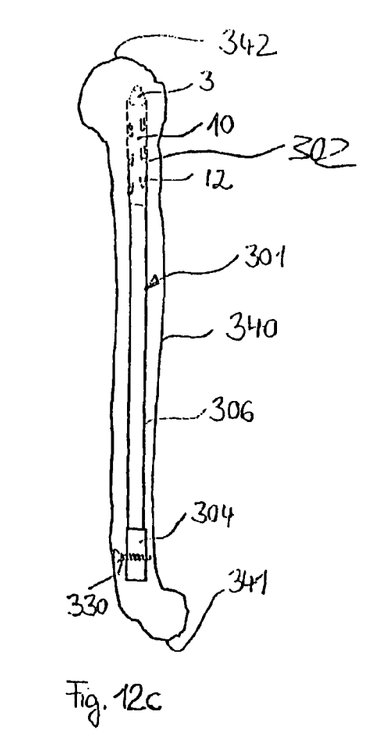

In the fourth embodiment shown in FIGS. 12a to 12c, those parts which correspond to the parts of the first embodiment are characterized with the same reference numerals. FIG. 12a shows the bone anchoring element 301 in use for stabilizing a femur 325. The bone anchoring element 301 comprises a first part 302 formed like the anchoring shaft of the bone anchoring element 1 of FIG. 1 having the barb elements 12 and a second part 306 which is cylindrical and has a head 304 adapted to receive a bone screw 330 at its end. For receiving the bone screw 330, the head 304 has a bore perpendicular to the main axis M of the bone anchoring element 301. The bone anchoring element 301 penetrates into the marrow cavity of the femur from its distal end 331 to its proximal end 332. The screw 330 assists in fastening the distal end of the bone to the bone anchoring element 301. The barb elements 12 anchor the bone anchoring element 301 in the bone. FIG. 12b shows an enlarged part of the bone anchoring element 301 and the proximal part of the femur. FIG. 12c shows the application of the bone anchoring element 301 according to the fourth embodiment in a humerus 340. As in the application in the femur, the bone anchoring element 301 extends from a distal end 341 to a proximal end 342 of the bone within the marrow cavity of the humerus. If the first part 302 is hollow, it is possible to fill it with bone cement or medical agents.

Modifications of the embodiments are possible. The head 4 needs not to be spherical segment-shaped but can have another shape, in particular, it can have any shape of known screw heads. The recesses 9 and the corresponding projections 11 need not to be U-shaped but can have a different shape. At least one recess and a corresponding projection is necessary to provide securing against rotation. However, it is also possible to prevent rotation by different means. For example, a pin which can be inserted into a transverse bore provided in the tubular body and the cylindrical shaft part 8 can be used.

The barb elements 12 need not have a quadrangular shape, but can have another shape as long as they have a free end and a base connecting the barb element to the shaft.

The bend in each barb element 12 defined by the line B was described to be angular. However, it is also possible that the bend is rounded. The barb elements 12 need not to be provided over the whole length of the tubular body 10 but can be provided also only in a section of the tubular body 10. The distance between the barb elements 12 may also vary. For certain applications only one single barb element 12 or one row of barb elements may be sufficient. The barb elements 12 need not to be evenly distributed but can be located at any place.

In yet another embodiment of the disclosure, if the tubular body 10 including the barb elements 12 is made from a shape memory alloy the tubular body 10 is treated before assembly of the bone anchoring element 1 in such a way that the barb elements 12 project at body temperature or at an elevated temperature and are in a collapsed position at a lower temperature, e.g. at room temperature. In operation the bone anchoring element 1 with collapsed barb elements 12 is pressed into the core hole 19. After the bone anchoring element 1 warms up and adapts to the body temperature or is heated through an external device, the barb elements 12 expand to their final position. This provides the advantage that it further reduces the amount of force required to press the bone anchoring element 1 into the core hole 19 and enables the adjustment of the bone anchoring element 1 to a desired depth by the sliding motion during its insertion as long as the barb elements 12 are in a collapsed state and do not press against the wall of the core hole 19. If the tubular body 10 has super elasticity in addition to shape memory characteristics, the higher elasticity of the barb elements 12 simplifies the handling and provides additional security in anchoring the bone anchoring element 1 in the bone.

It is possible that the tubular body 10 may include two or more individual sections having different characteristics or arrangements of barb elements.

In the disclosed embodiments, the tubular body 10 is made of one single tube. However, the tubular body 10 with sections having different characteristics of the barb elements 12 can be made of two separate tubes. In such a case, it is necessary to prevent rotation between the two tubes. This can be realized, for example, by providing recesses at the end of the first tube in which projections of the second tube engage.

The embodiments were described with a shaft formed by the tubular body 10 and the cylindrical shaft part. However, it is also possible that the shaft 2 includes a tubular body 10. Thus, the shaft 2 is hollow. In this case the tip and the head have to be directly connected to the tubular body 10. This can, for example, be made by a screw or a press fit joint.

It is also possible that the barb elements 12 are formed in plates, while these plates provided with the barb elements are attached to a shaft part 2, e.g. by accommodation in grooves formed in the shaft basis.

Figure 13A:
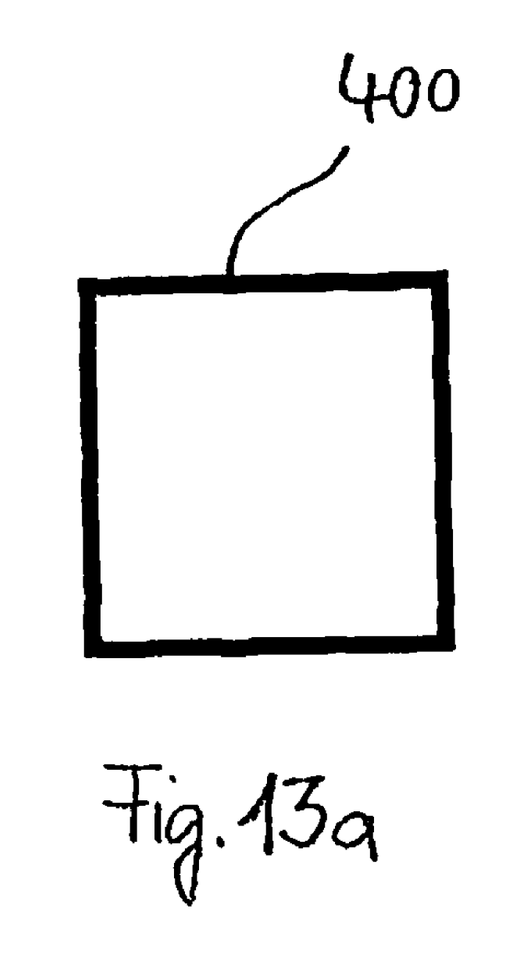
FIGS. 13a and 13b show further possibilities for the cross-sections of the bone anchoring element perpendicular to its main axis
Figure 13B:
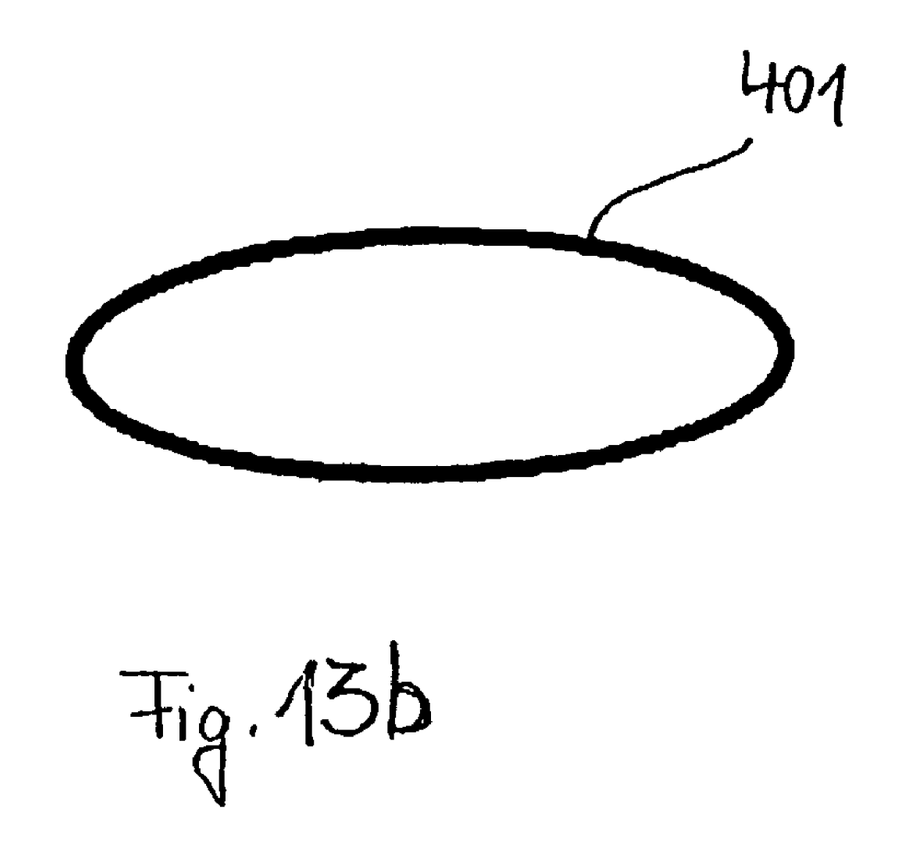

In the first and second embodiment, the shaft was described to have a circular cross-section perpendicular to its main axis and the third embodiment was described with a shaft having a rectangular cross-section perpendicular to its main axis. However, in case that the screw-like characteristic of the anchoring element 1 is not necessary the shaft 2 could also have any other cross-section like a square cross-section 400, as can be seen in FIG. 13a, or an ellipsoidal cross-section as can be seen in FIG. 13b. A core hole 19 having a corresponding cross-section is required. Such non-circular cross-section provides the advantage of higher resistance against torque. In all embodiments described above, the diameter of the tubular body 10 can vary over the axial length of the tubular body 10, for example it can decrease towards the tip so that the tubular body 10 has a conical outer surface.

The bone anchoring element 1 can be used together with a plate to establish a bone fixing device or with a receiver part to be connected with a rod to establish a spinal fixation system. Also, all further applications are conceivable in which the bone anchoring element 1 can be used instead of conventional bone screws or instead of conventional pins used in a bone anchoring manner.

While one or more embodiments of the disclosure has been illustrated and described, it will be apparent that various modifications can be made without departing from the spirit and scope of the disclosure. Accordingly, it is not intended that the disclosure be limited, except as by the appended claims.

What is claimed is:

1. A bone anchoring element comprising: a tubular body for anchoring in a bone and having two open ends; a cylindrical shaft inside the tubular body and assembled to the tubular body, and at least one barb element cut into the tubular body, the barb element having a free end and a base connecting the barb element to said tubular body, wherein the barb element has a first portion adjacent to the base and a second portion adjacent to the free end, and the second portion is inclined relative to the first portion in a direction radially outward from the tubular body; and wherein the barb element is bent at a bending line which is nearer to the free end than to the base, the first portion of the barb element extending from the base to the bending line and the second portion of the barb element extending from the bending line to the free end; wherein the first portion of the barb element is parallel to the longitudinal axis of the tubular body in an unbiased first position radially spaced apart from the cylindrical shaft when the cylindrical shaft is inside the tubular body; wherein the first portion of the barb element is movable from the unbiased first position to a biased second position wherein the first portion contacts the cylindrical shaft; and wherein the first portion of the barb element is elastically deformed in the second position.

2. The bone anchoring element of claim 1, wherein the second portion is bent relative the first portion in a direction radially outward from the tubular body.

3. The bone anchoring element of claim 1, wherein a bend of the first portion relative to the second portion at the bending line is an angular bend.

4. The bone anchoring element of claim 1, wherein a bend of the first portion relative to the second portion at the bending line is a rounded bend.

5. The bone anchoring element of claim 1, wherein the barb element has a free cutting edge, respectively, which includes an angle with a circular circumference line of the tubular body.

6. The bone anchoring element of claim 1, further comprising a plurality of barb elements.

7. The bone anchoring element of claim 6, wherein the barb elements are arranged along at least one helical line around the tubular body.

8. The bone anchoring element of claim 1, wherein the barb element is elastically deformable relative to the tubular body.

9. The bone anchoring element of claim 1, wherein said barb element is made of a shape memory alloy.

10. The bone anchoring element of claim 9, wherein the shape memory alloy comprises nitinol.

11. The bone anchoring element of claim 1, further comprising means for preventing rotation of said tubular body.

12. The bone anchoring element of claim 1, wherein the radial space allows the first portion to be elastically deformed and pivoted towards the cylindrical shaft.

13. The bone anchoring element of claim 1, wherein the barb element is spaced from the ends of the tubular body.

14. The bone anchoring element of claim 1: wherein an outer radius of the first portion of the barb element is equal to an outer radius of the tubular body at the base when the barb element is in the unbiased condition.

15. A method of anchoring a bone anchoring element in a bone, the bone anchoring element comprising a tubular body for anchoring in a bone and having two open ends, a cylindrical shaft inside the tubular body, and at least one barb element cut into the tubular body, the barb element having a free end and a base connecting the barb element to said tubular body, wherein the barb element has a first portion adjacent to the base and a second portion adjacent to the free end, and the second portion is inclined relative to the first portion in a direction radially outward from the tubular body, wherein the barb element is bent at a bending line which is nearer to the free end than to the base, the first portion of the barb element extending from the base to the bending line and the second portion of the barb element extending from the bending line to the free end, and wherein the first portion of the barb element is parallel to the longitudinal axis of the tubular body in an unbiased first position radially spaced apart from the cylindrical shaft when the cylindrical shaft is inside the tubular body, the method comprising: inserting the bone anchoring element into a core hole prepared in a bone such that the first portion of the barb element is inserted into the core hole before the second portion, a diameter of the core hole substantially corresponding to the diameter of the tubular body; and bending each barb element during insertion into the core hole from the unbiased first position wherein the barb element is spaced apart from the cylindrical shaft to a biased second position wherein the first portion of the barb element contacts the cylindrical shaft; turning the bone anchoring element after insertion of the bone anchoring element into the core hole in any one of a first direction and a second direction being opposite the first direction, the turning of the bone anchoring element in the first direction causing the tubular body to be moved in an insertion direction deeper in the core hole, and the turning of the bone anchoring element in the second direction causing the tubular body to be moved in the core hole opposite to the insertion direction; and wherein at least portions of the first portion and the second portion of the barb element is moveable from a first position inside the tubular body to a second position farther outward from the first position relative to the inside of the tubular body to prevent the bone anchoring element from being pulled out of the core hole.

16. A method of anchoring a bone anchoring element in a bone, the bone anchoring element comprising a tubular body for anchoring in a bone and having two open ends, a cylindrical shaft inside the tubular body, and at least one barb element cut into the tubular body, the barb element having a free end and a base connecting the barb element to said tubular body, wherein the barb element has a first portion adjacent to the base and a second portion adjacent to the free end, and the second portion is inclined relative to the first portion in a direction radially outward from the tubular body, wherein the barb element is bent at a bending line which is nearer to the free end than to the base, the first portion of the barb element extending from the base to the bending line and the second portion of the barb element extending from the bending line to the free end, and wherein the first portion of the barb element is parallel to the longitudinal axis of the tubular body in an unbiased first position radially spaced apart from the cylindrical shaft when the cylindrical shaft is inside the tubular body, the method comprising:
  inserting the bone anchoring element into a core hole prepared in a bone such that the first portion of the barb element is inserted into the core hole before the second portion, a diameter of the core hole substantially corresponding to the diameter of the tubular body;
  bending the first portion of each barb element during insertion into the core hole from the unbiased first position wherein the first portion is spaced apart from the cylindrical shaft to a biased second position wherein the first portion of the barb element contacts the cylindrical shaft; and
  bending the second portion of each barb element toward the cylindrical shaft after the bending of the first portion, the bending of the second portion being relative to the first portion about a bending line between the first portion and the second portion.

17. A bone anchoring element comprising: a tubular body having a first end and a second end; a tip coupled to the first end of the tubular body; and a head coupled to the second end of the tubular body and having a larger diameter than a largest diameter of the tip, a cylindrical shaft insertable inside the tubular body; and at least one barb element cut into the tubular body, the barb element having a free end, a base connecting the barb element to said tubular body, and a bending line between the base and the free end, wherein a first portion of the barb element extends from the base to the bending line, and a second portion of the barb element extends from the bending line to the free end; wherein, when the barb element is in an unbiased position with the cylindrical shaft inside the tubular body, the first portion of the barb element is parallel to a longitudinal axis of the tubular body and the second portion is inclined relative to the first portion in a direction radially outward from the tubular body at the bending line; wherein the first portion of the barb element is movable from the unbiased first position to a biased second position wherein the first portion contacts the cylindrical shaft; and wherein, the first portion of the barb element is closer to the tip than the second portion of the barb element.

18. The bone anchoring element of claim 17, wherein the first portion of the barb element is movable from the unbiased position to a biased position, wherein the barb element is elastically deformed in the biased position.

19. The bone anchoring element of claim 17, wherein the bending line is nearer to the free end than to the base.

* * * * *